(12) United States Patent
Chang

(10) Patent No.: US 6,640,126 B2
(45) Date of Patent: Oct. 28, 2003

(54) ACOUSTIC GATING MONITOR FOR MAGNETIC RESONANCE IMAGING SYSTEM

(75) Inventor: Hsu Chang, Fremont, CA (US)

(73) Assignee: Toshiba America MRI, Inc., Fremont, CA (US)

( * ) Notice: Subject to any disclaimer, the term of this patent is extended or adjusted under 35 U.S.C. 154(b) by 41 days.

(21) Appl. No.: 09/791,882

(22) Filed: Feb. 26, 2001

(65) Prior Publication Data

US 2002/0120190 A1 Aug. 29, 2002

(51) Int. Cl.$^7$ ............................................... A61B 5/05
(52) U.S. Cl. ....................................................... 600/413
(58) Field of Search ................................ 600/413, 415, 600/410, 407, 419

(56) References Cited

U.S. PATENT DOCUMENTS

| | | | |
|---|---|---|---|
| 4,777,957 A | * 10/1988 | Wehrli et al. ............... 600/413 |
| 4,804,054 A | 2/1989 | Howson et al. |
| 4,878,499 A | 11/1989 | Suzuki et al. |
| 4,903,703 A | * 2/1990 | Igarashi et al. ............. 600/418 |
| 4,938,230 A | 7/1990 | Machek et al. |
| 4,951,679 A | 8/1990 | Harada |
| 4,971,043 A | 11/1990 | Jones |
| 5,009,644 A | 4/1991 | McDonald |
| 5,038,785 A | * 8/1991 | Blakeley et al. ............. 600/484 |
| 5,074,309 A | * 12/1991 | Gerdt ......................... 600/528 |
| 5,139,026 A | 8/1992 | Niwa |
| 5,184,074 A | 2/1993 | Arakawa et al. |
| 5,222,491 A | * 6/1993 | Thomas ................. 128/205.13 |
| 5,223,828 A | 6/1993 | McKiel, Jr. |
| 5,239,265 A | 8/1993 | Sugahara |
| 5,287,102 A | 2/1994 | McKiel, Jr. |
| 5,363,844 A | 11/1994 | Riederer et al. |
| 5,450,852 A | 9/1995 | Archibald et al. |
| 5,451,924 A | 9/1995 | Massimino et al. |
| 5,464,014 A | 11/1995 | Sugahara |
| 5,497,779 A | 3/1996 | Takaya et al. |
| 5,590,060 A | 12/1996 | Granville et al. |
| 5,709,207 A | 1/1998 | Duerk et al. |
| 5,771,893 A | * 6/1998 | Kassai et al. ............... 600/419 |
| 5,797,850 A | 8/1998 | Archibald et al. |
| 5,821,748 A | 10/1998 | Gatehouse |
| 5,833,608 A | * 11/1998 | Acker ......................... 600/409 |
| 5,836,887 A | 11/1998 | Oka et al. |
| 5,853,005 A | * 12/1998 | Scanlon ....................... 600/459 |
| 5,876,346 A | 3/1999 | Corso |
| 5,897,496 A | * 4/1999 | Watanabe .................... 600/413 |
| 5,919,141 A | * 7/1999 | Money et al. ............... 600/513 |
| 5,928,148 A | * 7/1999 | Wang et al. ................. 600/420 |
| 5,941,828 A | 8/1999 | Archibald et al. |
| 5,944,023 A | 8/1999 | Johnson et al. |
| 5,975,078 A | * 11/1999 | Pauley ................... 128/205.23 |
| 6,009,341 A | * 12/1999 | Edelman ...................... 600/413 |
| 6,226,543 B1 | * 5/2001 | Gilboa et al. ................ 600/407 |
| 6,311,085 B1 | * 10/2001 | Meaney et al. .............. 600/420 |
| 6,418,336 B1 | * 7/2002 | Kimmlingen et al. ........ 600/410 |
| 6,425,864 B1 | * 7/2002 | Foo et al. .................... 600/420 |

* cited by examiner

Primary Examiner—Daniel Robinson
(74) Attorney, Agent, or Firm—Nixon & Vanderhye P.C.

(57) ABSTRACT

An MRI imaging system provides an audible feedback signal in the gantry room triggered by a physiological sensor on the patient. The feedback signal is a sound generated by one of the MRI gradient coils. The sensor output signal may be indicative of the patient's heartbeat, or other physiological event. The application of the sequence causes the coil to emit a sound that is associated with the sensor output signal.

8 Claims, 1 Drawing Sheet

US 6,640,126 B2

ACOUSTIC GATING MONITOR FOR MAGNETIC RESONANCE IMAGING SYSTEM

FIELD OF THE INVENTION

This invention relates generally to magnetic resonance (MR) imaging techniques. In particular, the invention relates to MR imaging that is triggered and/or synchronized with patient sensors that detect physiological conditions, such as a heartbeat, blood pulse, or respiration of the patient being imaged.

BACKGROUND OF THE INVENTION

Magnetic Resonance Imaging (MRI) is a widely accepted and commercially available technique for obtaining digitized visual images representing the internal structure of objects (such as the human body) having substantial populations of atomic nuclei that are susceptible to nuclear magnetic resonance (MR) phenomena. In MRI, nuclei in the body of a patient to be imaged are polarized by imposing a strong main magnetic field ($B_0$) on the nuclei. The nuclei are excited by a radio frequency (RF) signal at characteristic MR (Lamor) frequencies. By spatially distributing localized magnetic fields surrounding the body and analyzing the resulting RF responses from the nuclei, a map or image of these nuclei responses as a function of their spatial location is generated and displayed. An image of the nuclei responses provides a non-invasive view of a patient's internal organs and of other tissues.

As shown in FIG. 1, an MR imaging system typically includes a magnet 10 to impose the static magnetic field ($B_0$), gradient coils 12 for imposing spatially distributed gradient magnetic fields ($G_x$, $G_y$, and $G_z$) having gradients along three respective orthogonal coordinates, and RF coils 14 and 16 to transmit and receive RF signals to and from selected nuclei of the body being imaged. The patient 18 lies on a patient table 20 such that a portion of the patient to be imaged is moved, in three-dimensions, into an "imaging volume" between the magnet and coils, which defines a field of view (FOV) of the MRI system. One or more sensors, such as electrocardiogram (EKG) sensor 21, may be positioned on the patient to monitor physiological conditions of the patient, such as the heartbeat.

The MRI system operator controls the system through a computer workstation 22 with a keyboard, screen and other operator input/output devices. The MRI system operator positions the patient within the imaging volume using a movable table 20, and may attach sensors 21 that monitor the patient during imaging.

Sensors 21 monitor the heartbeat, respiration, blood pulse and/or other physiological conditions of the patient. Signals generated by these sensors may be applied by the MRI system to trigger or synchronize MR imaging with the physiological condition(s) being monitored. For example, a heartbeat sensor generates a signal indicative of the patient's heartbeat that is applied to trigger an MR imaging sequence synchronized with the beating heart. Synchronization of an MR image with a beating heart may improve the clarity of an still image of the beating heart or enable a real-time image of the heart. Similarly, sensors monitoring physiological conditions may be used to synchronize MR imaging with respiration, blood pulses, and other conditions of the patient. The signal from the monitor may also be recorded synchronously with the image data and used for post-processing.

Sensors to monitor physiological conditions are well known. For example, EKG electrical sensors mounted on a patient's skin detect electrical signals from the heart and generate signals indicative of the heartbeat. Fluid flow sensors mounted near the nose or mouth of a patient detect a patient's breath and generate a respiration signal. Similarly, electromechanical sensors mounted on the chest or back of a patient detect changes in the shape of the abdomen to generate signals indicative of the respiration of the patient. Blood pulse can be detected by light sensors that detect light reflected from skin or by pressure sensors that detect pressure changes in an inflated bladder wrapped around the patient's arm.

The placement of such sensors on the patient's body can be critical. If the sensor is not placed optimally, then the triggering of MRI scans can be affected. For example, the analog signal generated by the sensor might be of insufficient magnitude to even pass through a detection threshold. Alternatively, the passage through a preset threshold may be incorrectly timed and/or unreliable. Thus, the sensor placement should be checked for correctness before expensive and time consuming actual MRI scans are conducted.

Providing an audio and/or visual signal feedback indicative of proper sensor placement on a patient prior to MR imaging can be difficult. MR imaging is extremely sensitive to stray electromagnetic emissions. Such emissions may be emitted by signal wires and circuits associated with sensors. To reduce interference due to extraneous emissions, wires and circuits within the MRI imaging room and especially near the patient are minimized. In particular, the wires within the MR imaging room are preferably limited to only those wires needed for the gradient coils and the RF coils. Other signal wires and circuits are generally precluded from the MR imaging room.

Conventional CRT oscilloscopes that are often used to provide a visual feedback of patient sensor placement cannot be used in the presence of the strong $B_0$ magnetic field within an MRI gantry room. In addition, the additional wires and circuits associated with the oscilloscope may, if left in the gantry room, cause unnecessary interference with the MRI process—and thus must typically be located in an inconvenient place outside the gantry room. Similar problems of inconvenience occur if an MRI system monitor outside the gantry room is utilized to monitor sensor placement. Moreover, even if the oscilloscope or MRI system monitor were used, it would add to the cost of the MRI system. Still further, to view an auxiliary monitor, its visual display requires that an operator turn away from the MRI imaging screen to determine whether the sensor is properly placed and functioning. Thus, while in-room monitors have been developed for MRI systems, (See U.S. Pat. No. 5,184,074, issued to Kaufman et al.) they have various disadvantages such as cost, complexity and possible stray RF emissions.

In MRI it is sometimes desirable to trigger or synchronize the image acquisition sequence with a physiologically generated signal, such as the heartbeat, the blood pulse or the respiration. The typical MRI system provides an input where a digital ON-OFF signal is used to create within the machine such triggering or synchronization.

To generate this digital signal, an analog signal is first created by direct monitoring of the physiologic process of interest. Examples are EKG detection for the heartbeat, breath or abdomen shape for breathing, and pressure or reflected light for blood flow. The signal these processes create is continuous, and a trigger level or threshold has to be set to extract from them a desired ON-OFF signal.

The analog detection devices are attached to the body or otherwise interact with it, and because of patient-to-patient variability, operators need to locate them in certain ways, or need to test different locations to get a reliable signal. Thus, the signal needs to be monitored. This is typically done with an oscilloscope or by digitizing the continuous signal and displaying it on the MRI console monitor.

Oscilloscopes themselves need adjustment that is sometimes beyond the capabilities of the MRI operators, they add cost, and they do not work near the MRI magnets. The console display is reliable and simple, but requires that the operator move between the patient and the console, which is in a different room. This adds time to the setup process. An in-room monitor for real time display (U.S. Pat. No. 5,184,074) could be used to display the signal, but it adds cost.

There is a long-felt need for an economic device that provides sensor signal feedback, such as of an EKG heartbeat signal, to an MRI technician within the MRI gantry room. It is desirable that this device not add extra wires and circuits, especially within the MR imaging room.

SUMMARY OF THE INVENTION

This invention provides immediate real-time feedback to an operator of an MRI apparatus as to the adequacy of the placement of a physiologic sensor on a patient being prepared to undergo MRI. Basically, a special imaging sequence—one not actually used for producing any image data and perhaps consisting only of a single pulse of a single gradient coil—is gated (i.e., triggered) by the occurrence of a specific physiological phenomenon detected by a sensor placed on the patient. Since gradient coils typically produce a characteristic sharp noise when they are pulsed, the triggering of the special imaging sequence results in the production of an immediately noticeable and readily identifiable sound.

In practice, the physiological phenomenon-gated special imaging sequence mode is initiated just prior to placement of the sensor on the patient. The operator is then free to test different placements of the sensor. If the sensor is improperly placed, the special imaging sequence will not be triggered and the characteristic gradient coil noise will not be produced.

When the sensor is properly placed, however, and the special imaging sequence is properly triggered by the desired physiological process of the patient, the characteristic sound of the gradient coil noise will be audible and will follow the rhythm of the patient's physiological process. In this manner, as the operator adjusts the sensor placement, the triggered imaging sequence sounds can be used as real-time audible feedback to guide the operator as to the adequacy and reliability of the selected physiological process or placement of the sensor. In addition, the method of the present invention may be easily implemented on most types of MRI equipment for little or no additional expense.

The present invention provides an essentially zero cost feedback signal for determining optimism positioning of sensors in an MRI gantry room. The invention does not add any wires or circuits to the MRI system, because it uses only an existing MRI gradient coil to generate an audible sound—triggered by the sensor as currently applied to a patient. Because it relies on an existing MRI system coil, the invention is inexpensive (especially in view of conventional oscilloscope feedback devices). Moreover, the invention provides an audible sound that was directly triggered by a heartbeat or other physiological condition. This immediately and clearly notifies the MRI technician performing the placement that the sensor is properly positioned and functioning—or, by its absence, that the sensor is not properly detecting the heartbeat or other physiological condition.

During this preparatory stage, the sensor signal is used by the MRI system to immediately trigger a special truncated test gated or triggered sequence, e.g., single pulse, applied to one of the gradient coils. This causes the gradient coil to vibrate, e.g., "ring", and generate a distinct sound that can be readily heard by the MRI operator in the gantry room. If the sensor is improperly placed or is malfunctioning, then it will not trigger the special test sequence and there will be no distinct sound from the gradient coil.

Obtaining good triggering signals from sensors applied to a patient can be problematic. To obtain a good signal, the sensors must be properly positioned on the patient. Positioning sensors on the patient to detect physiological conditions generally requires that the MRI system operator be able to see or hear a characteristic trigger signal generated by the sensor as feedback to the sensor positioning process. By hearing or seeing such a trigger signal indication from the sensor, the operator can determine when the sensor is properly placed on the patient. For example, EKG sensors must be positioned on the patient so as to properly detect electrical signals from the heartbeat. To determine whether the sensors are properly positioned, the operator places the sensors on the patient's chest in the expected vicinity of where the sensors can detect a heartbeat signal. The sensors may be connected to an EKG monitor so that the operator can then see or hear the heartbeat signal being detected by the sensors. If the signal is not clear and/or strong, the operator can move the sensors around on the chest until the detected EKG signal is strong and clear. Similarly, before a sensor-triggered MRI scan is conducted, the technician placing the sensor(s) on the patient in the MRI gantry room needs to have feedback to be sure that the sensor(s) is (are) properly placed. With this invention such feedback is provided by audible signals conveniently and immediately in the gantry room and at essentially zero added cost. Thus, the technician does not need to go back and forth between the patient and a monitor outside the gantry room.

The acoustic gated monitor is only used during patient setup. The operator has to be in the room for setting up the sensor system, e.g., EKG, finger plethismograph, pressure cuff, breath flow, whatever. This requires adjusting for picking up a physiologic signal. How does the operator know if the placement is correct? Having an oscilloscope in the room is inconvenient: if it is not shielded it has to be brought in for the setting up and taken out before imaging starts, and the magnetic field affects it. Going out to look at the console monitor is very inconvenient looking at a scope that is a distance from the magnet while playing with the patient sensor in or near the magnet is inconvenient. So the operator turns on one (or more) gradient sequence (without RF to cause interference) and listens as sensor adjustments are made. The operator positions the sensor on the patient. When the sensor is correctly positioned, the gated pulses to the coils generate sounds heard by the operator. These sounds inform the operator that the sensor is properly positioned. Once the proper positioning of the sensors is confirmed by the sounds from the coil, the operator leaves the gantry room and starts a conventional imaging sequence.

BRIEF DESCRIPTION OF THE DRAWINGS

The purpose and advantages gained by the present invention will be understood by careful study of the following detailed description of a presently preferred exemplary embodiment with particular reference to the accompanying drawings, of which.

DETAILED DESCRIPTION OF A PRESENTLY PREFERRED EXEMPLARY EMBODIMENT

Figure 1:
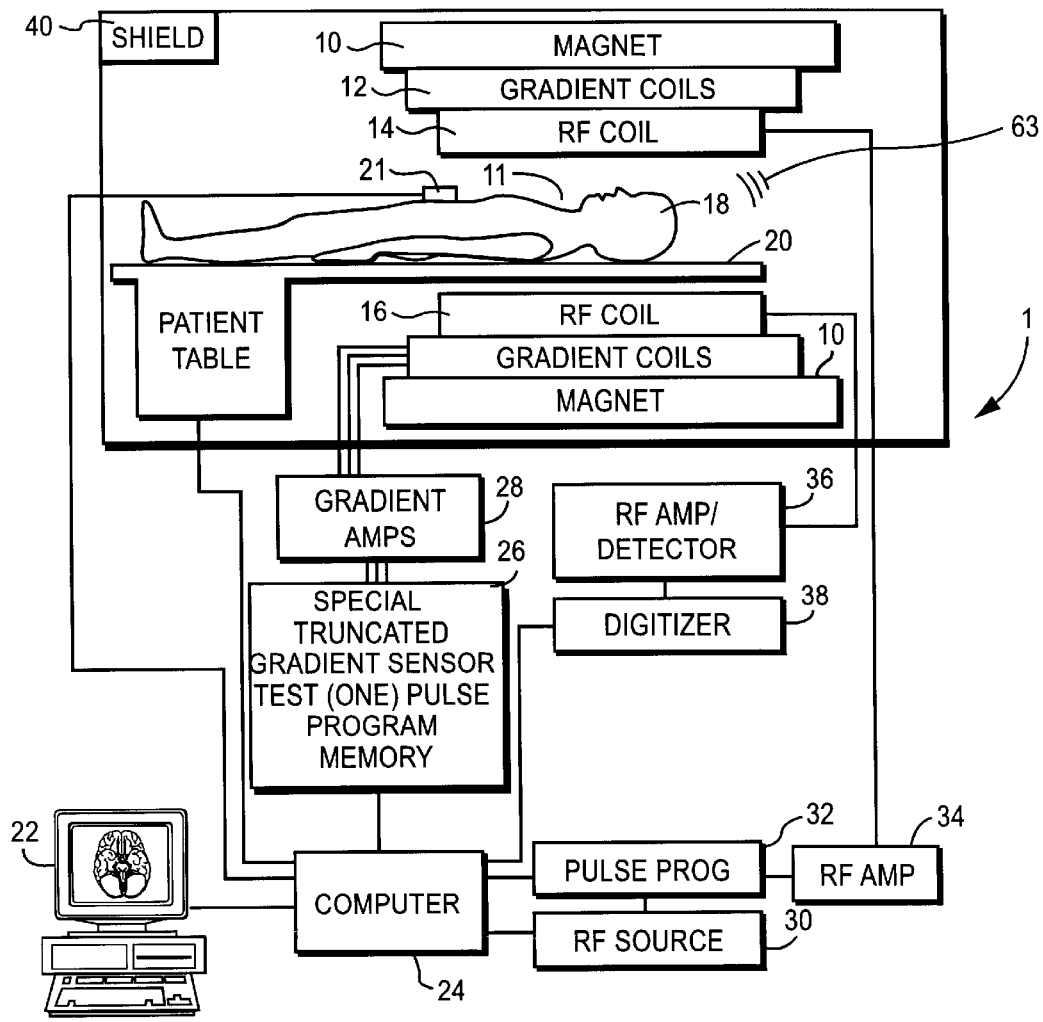
FIG. 1 is a schematic diagram of an exemplary MRI system employing this invention.
Figure 2:
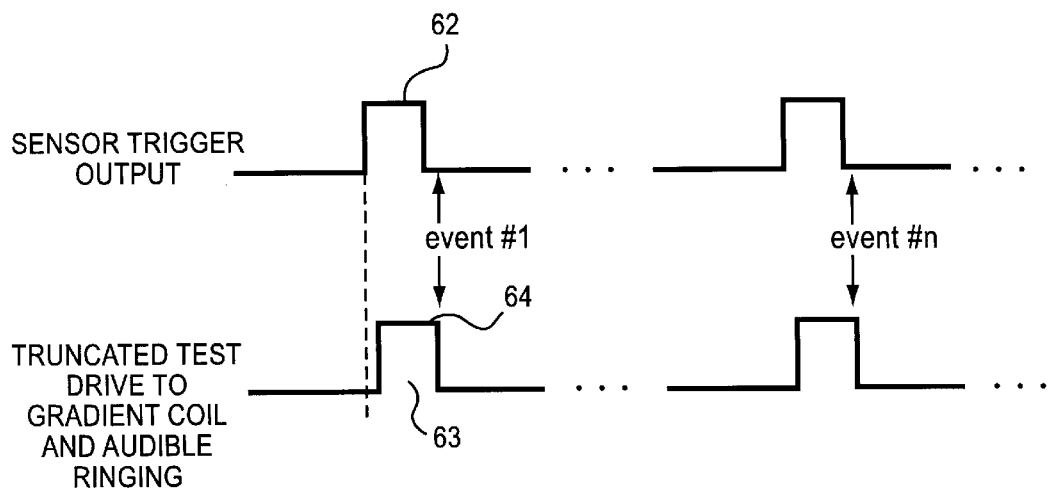
FIG. 2 is a gradient pulse timing diagram of an exemplary test gradient pulse sequence triggered by a sensor signal for the system of FIG. 1.

FIG. 1 depicts an MRI system 1, such as the Toshiba OPART™ MRI system. An MRI system may comprise a large polarizing magnet structure 10 which generates a substantially uniform homogeneous polarizing static magnetic field ($B_0$) surrounding a patient imaging volume 11. A suitable carriage, e.g., patient table 20, inserts a portion of the anatomy of the patient 18 within the image volume 11. A sensor 21 may be applied to the patient 18 so as to detect a physiological condition of the patient, such as heartbeat, respiration and/or blood pulses flowing through the circulatory system. The patient, patient table (bed) 20, magnet 10, and coils 12, 14, 16 are housed in a shielded gantry room 40 that is isolated from external RF and electromagnetic interference. From this room, a technician prepares the patient for imaging, positions the patient on the bed and attaches sensors to the patient. The technician generally does not have monitoring electronics, such as a computer display screen, available in the gantry room. Monitoring electronics can generate RF signals that would interfere with MR imaging and/or such monitoring equipment (e.g., a CRT) may be inoperative in the presence of the strong polarizing magnetic field $B_0$. Thus, proper positioning of the sensor 21, without this invention, can become an awkward, tedious task requiring iterative sensor positioning and walking to/from the monitor outside the gantry room. This invention eliminates such problems. Once the patient is prepared for imaging, the technician/operator exits the gantry room 40 and controls the imaging sequence from a workstation 22.

Gradients in $B_0$ are selectively created by electromagnetic gradient coils 12 that are operated by an MRI sequencing processor 26. RF nuclei nutation pulses are transmitted into patient tissue within the image volume by RF coil 14. RF responses constituting the MR signal are received from the patient tissue via suitable RF detection coils 16.

The MRI system operator controls the system 1 through a computer workstation 22 with a keyboard, screen and other operator input/output devices. The workstation is generally located outside of the shielded imaging room 40. The MRI workstation 22 is electronically connected to an MRI system computer 24 which controls the MRI system. The computer converts operator MRI image sequence parameter selections into suitable commands for operation of the MRI system. In particular, the computer controls the selection of an appropriate gradient pulse program module 26 (e.g., from an associated memory device) which, in turn, applies a selected magnetic pulse sequence(s) to the gradient amplifiers 28 that drive the gradient coils. The MRI pulse sequences may be triggered by a sensor output signal.

In this invention, a special truncated test sequence may be selected for use during patient setup that causes the computer 24 to command the pulse program module 26 to apply a non-imaging pulse sequence (e.g., of one immediate pulse) to one of the gradient coils 12 for the sole purpose of causing the coil to vibrate and emit a sound that coincides with the currently available trigger sensor output, if any.

Since the generation of a truncated (e.g., single) pulse sequence is considerably more simple than that of a traditional MRI pulse sequence, it is not necessary to further describe the exemplary simple software for implementing such a test mode of operation. Those in the art will have no difficulty devising a suitable truncated test sequence in a suitable portion of the MRI system memory.

In an MRI system, various coils produce RF excitation pulses and accompanying gradient field pulses result in and acquire an MR signal during an MRI "acquisition sequence" using well-known MRI techniques. Each acquisition sequence (or series of sequences) may be triggered by an event, such as a heartbeat signal from an EKG sensor 21 (FIG. 1).

The physiological sensor 21 applied to the patient monitors a condition, such as the patient's heartbeat, respiration, and/or blood pulse in the circulatory system. As the sensor detects the occurrence of the heartbeat, respiration or blood pulse, if properly placed, it generates a sensor trigger signal 62 to the MRI computer 22. The computer 22 may apply the sensor signal to trigger an MRI acquisition sequence or to inhibit an acquisition sequence. For example, an EKG signal may be used to trigger a sequence where the sequence is to correspond to the heartbeat. In another example, a respiration signal may be used to inhibit an acquisition sequence where a patient's movement during respiration might blur an image.

However, in the invention, a special sensor test mode is provided wherein a gradient pulse 64 is applied to acoustically "ring" one or more of the gradient coils. This test "ring" pulse is triggered (gated) by a sensor signal 62 that is generated, e.g., by a heartbeat sensor, positioned on the patient. The audible sound 63 caused by gradient pulse 64 then immediately notifies the MRI system technician/operator in the gantry room (or elsewhere) that the heartbeat sensor is functioning properly and is detecting a heartbeat signal. If the operator does not periodically, e.g., once every 1/60th of a second in time with a manually-detected patient pulse, hear an audible ring 63 from the gradient coil, then the operator can assume that the heartbeat is not being properly detected by the sensor. The operator can then decide whether the sensor should be repositioned or otherwise serviced.

The use to which the sensor signal is applied will depend on the type of signal, e.g., EKG heartbeat signal, respiration and blood pulse, and the mode of MRI operation selected by the operator. Moreover, in the initial test mode, only a non-imaging sequence (intended to only generate an audible sound) need be triggered by the sensor. In particular, upon receipt of a sensor trigger signal 62, the computer 22 may cause the gradient pulse program module 26 to generate a special test pulse sequence 64 that causes one of the gradient coils to vibrate ("ring") and thereby create an audible sound. This sound may be heard by the MRI system operator as an indication that the sensor is properly detecting the desired physiological condition of the patient.

The test sequence may have no purpose other than to audibly ring the gradient coil, and may not influence the regular MRI pulse sequences. Indeed, the gradient pulse 64 may be applied without any radio frequency (RF) pulses. Generally, there will be no imaging while the operator is prepping the patient on bed 20 in the gantry room. Thus, there would typically be no need or desire to apply full MRI pulse sequences (e.g., including RF pulses) to the coils of the MRI system.

The noise caused by vibration of the gradient coil is a common, normally adverse, side effect of applying pulse sequences to gradient coils. However, the present invention make constructive use of such coil sounds by providing those sounds as audible feedback from a sensor 21 trigger output.

After a patient has been prepared for imaging and sensors have been properly placed on the patient (using the coil sounds generated by the present invention), the operator leaves the MRI gantry room and enters the MRI control room. From the control room, the operator initiates and controls MR imaging as usual and conventional.

While the invention has been described in connection with what is presently a preferred exemplary embodiment, it is to be understood that the invention is not to be limited to the disclosed exemplary embodiment, but on the contrary, is intended to cover all modifications and variations of the invention apparent to those skilled in the art from this disclosure, including those coming within the scope of the following appended claims.

What is claimed is:

1. A method for magnetic resonance imaging (MRI) using an MRI system having at least one coil, said method comprising:
   a. positioning a patient within the MRI system for MR imaging;
   b. coupling a sensor to the patient and providing a sensor output signal representing a physiological event in the patient; and
   c. applying at least one electrical pulse to the at least one coil triggered by said output signal of the sensor, and thereby emitting an audible sound from the at least one coil.

2. A method as in claim 1 further comprising adjusting the sensor on the patient if the sensor does not reliably trigger said audible sound.

3. A method as in claim 1 wherein the physiological event is a heartbeat, the sensor detects the heartbeat, and the audible sound coincides with the heartbeat.

4. A method as in claim 1 wherein the coil is a magnetic gradient field coil.

5. A method as in claim 1 wherein the sensor detects patient respiration as the physiological event, and the audible sound coincides with the patients respiration.

6. A method as in claim 1 wherein the sensor detects a blood flow pulse in the patient as the physiological event, and the audible sound coincides with the patient's blood flow pulse.

7. A method for magnetic resonance imaging (MRI) using an MRI system having at least one coil, said method comprising:
   a. positioning a patient within the MRI system for MR imaging;
   b. coupling a sensor to the patient such that the sensor detects a recurring physiological event in the patient;
   c. generating a sensor output signal when the sensor detects the physiological event in the patient;
   e. applying the sensor output to generate at least one electrical pulse to the at least one coil, and
   f. emitting an audible sound from the at least one coil due to the application of the pulse, wherein the sound coincides with the physiological event.

8. A method as in claim 7 wherein said electrical pulse is unrelated to pulses applied to said at least one coil to generate an image of the patient.

* * * * *